United States Patent
Dolliver et al.

(10) Patent No.: US 8,157,792 B2
(45) Date of Patent: Apr. 17, 2012

(54) WOUND DRAINAGE SUCTION RELIEF

(75) Inventors: Phillip B. Dolliver, Framingham, MA (US); Alec Bobroff, Norfolk, MA (US)

(73) Assignee: Haemonetics Corporation, Braintree, MA (US)

( * ) Notice: Subject to any disclaimer, the term of this patent is extended or adjusted under 35 U.S.C. 154(b) by 829 days.

(21) Appl. No.: 10/787,849

(22) Filed: Feb. 26, 2004

(65) Prior Publication Data

US 2005/0192548 A1 Sep. 1, 2005

(51) Int. Cl.
*A61M 27/00* (2006.01)
*A61M 31/00* (2006.01)
*A61M 1/30* (2006.01)
*A61M 25/00* (2006.01)

(52) U.S. Cl. ........ 604/543; 604/93.01; 604/19; 604/523

(58) Field of Classification Search .................... 604/22, 604/35, 48, 176, 290, 293, 523, 541–543, 604/335, 902, 19, 93.01, 317
See application file for complete search history.

(56) References Cited

U.S. PATENT DOCUMENTS

| | | | |
|---|---|---|---|
| 3,589,363 A * | 6/1971 | Banko et al. | 604/22 |
| 4,141,361 A | 2/1979 | Snyder | 128/278 |
| 4,460,354 A | 7/1984 | Weilbacher et al. | 604/73 |
| 4,534,765 A | 8/1985 | Todd et al. | 604/321 |
| 4,664,652 A | 5/1987 | Weilbacher | 604/133 |
| 4,994,022 A | 2/1991 | Steffler et al. | 604/7 |
| 5,616,121 A * | 4/1997 | McKay | 604/35 |
| 5,645,540 A | 7/1997 | Henniges et al. | 604/320 |
| 5,733,253 A | 3/1998 | Headley et al. | 604/4 |
| 5,853,382 A | 12/1998 | Kingsley et al. | 604/4 |
| 6,017,493 A * | 1/2000 | Cambron et al. | 422/44 |
| 2002/0026946 A1 * | 3/2002 | McKay | 128/898 |
| 2004/0064132 A1 * | 4/2004 | Boehringer et al. | 604/543 |

* cited by examiner

*Primary Examiner* — Jackie Ho
*Assistant Examiner* — Bradley Thomas, Jr.

(57) ABSTRACT

In accordance with one embodiment of the invention, there is provided a wound drainage system for draining fluid from a wound of a patient. The system includes a drain catheter. A suction means applies suction at the drain catheter such that fluid is drawn from the wound. While drawing fluid from the wound, a controller periodically increases and decreases the application of suction at the drain catheter. This allows the tissue surrounding the wound drain to relax, thus preventing obstruction of the drain catheter.

23 Claims, 2 Drawing Sheets

US 8,157,792 B2

WOUND DRAINAGE SUCTION RELIEF

TECHNICAL FIELD

The present invention generally relates to a device for providing drainage of a wound and more particularly, to a device that periodically increases and decreases the application of suction at a drain catheter.

BACKGROUND ART

It is often desirable to drain fluids from a wound. Fluids that can accumulate in the wound and lead to various complications include blood, serum, pus, bile or other biological fluids. Removal of these fluids can promote proper healing and reduce the threat of infection, thus reducing the amount of time spent in the hospital.

A drain catheter can be used to drain fluids from the wound. The drain catheter typically includes a plastic tube having one or more perforations at one end. The perforated end of the tube is placed adjacent the wound, while the other end of the tube may be connected to a source of suction, which is typically wall suction present in an operating room. The suction causes fluid to be aspirated from the wound, whereupon it can be collected in a suitable container.

A problem arising when using a drain catheter is that the tube perforations may become occluded, preventing further drainage of fluid. Due to the close proximity of tissue to the drain catheter, tissue may be drawn towards the catheter and expand into the tube perforations, blocking the passage of fluids into the tube. Debris such as a blood clot or a coagulated protein mass may further block the tube perforations.

If the occluded drain catheter is not cleared in a timely manner, fluid in the wound may accumulate, slowing the healing process and/or causing infection, as described above. Additionally, an operator of the drain catheter may observe the lack of fluid coming from the occluded drain catheter and wrongly believe that no more fluid remains in the wound. This may cause the operator to prematurely remove the drain catheter from the wound. Furthermore, due to the ingrowth of tissue, more force may be needed to adjust or remove the drain catheter, causing additional trauma to the wound.

SUMMARY OF THE INVENTION

In accordance with one embodiment of the invention, there is provided a wound drainage system for draining fluid from a wound of a patient. The system includes a drain catheter. A suction means applies suction at the drain catheter such that fluid is drawn from the wound. While drawing fluid from the wound, a controller periodically increases and decreases the application of suction at the drain catheter. This allows the tissue surrounding the wound drain to relax and move away from the drain catheter, relieving and/or preventing obstruction of the drain catheter. Complete drainage of the wound can thus be achieved.

In related embodiments of the invention, the controller may include a computer readable medium encoded to perform a method that includes periodically increasing and decreasing the application of suction at the drain catheter. The controller may periodically control the application of suction at the drain catheter such that suction is applied at the drain catheter for a first predetermined amount of time, and interrupted at the drain catheter for a second predetermined amount of time. The suction means may include wall suction available from a facility wide system or a separate pump associated with the drainage system. To control the application of suction at the drain catheter, the controller may control a valve means, such as a vent valve, positioned between the drain catheter and the suction means. The valve means may be disposed in, without limitation, a conduit in fluid communication with the suction means and the drain catheter. In other embodiments, the controller may control the suction means. For example, the suction means may include a pump which the controller regulates, such as by periodically interrupting turning the pump on and off. The pump may provide a partial or full vacuum.

In accordance with another aspect of the invention, a computer program product for use on a computer system for controlling a wound drainage system is provided. The wound drainage system includes a drain catheter and suction means, the suction means for applying suction at the drain catheter. The computer program product includes a computer usable medium having computer readable program code thereon. The computer readable program code includes program code for periodically increasing and decreasing the application of suction at the wound drain catheter.

In related embodiments of the invention, the program code may periodically apply suction at the drain catheter for a first predetermined amount of time and interrupt suction at the drain catheter for a second predetermined amount of time. The program code may control a valve, such as a vent valve, positioned between the suction means and the drain catheter. In other embodiments, the program code may control the suction means, which may be a pump. For example, the program code may periodically turn on and off the pump.

In accordance with still another aspect of the invention, a wound drain system for implantation into and for drainage of fluid from a wound of a patient is provided. The system includes a drain catheter in fluid communication with a suction device via a conduit. A valve, such as a vent valve, may be positioned between the suction means and the drain catheter. The valve may be, for example, disposed in the conduit. A controller variably controls the valve to periodically increase and decrease the application of suction at the drain catheter.

In related embodiments of the invention, the controller controls the valve to periodically apply suction at the drain catheter for a first predetermined amount of time and interrupts suction at the drain catheter for a second predetermined amount of time. The suction device may be a pump. The controller may include a computer readable medium encoded to perform a method for controlling the valve so as to periodically increase and decrease the application of suction at the drain catheter.

In accordance with yet another embodiment of the invention, a wound drainage system for draining fluid from a wound of a patient includes a drain catheter and a suction source for applying suction at the drain catheter. A controller controls the suction source so as to periodically increase and decrease the application of suction at the drain catheter.

In related embodiments of the invention, the controller may control the suction source to periodically apply suction at the drain catheter for a first predetermined amount of time and interrupts suction at the drain catheter for a second predetermined amount of time. The suction source may be a pump. The controller may, without limitation, control the pump to periodically turn on and off. The controller may include a computer readable medium encoded to perform a method for controlling the suction source so as to periodically increase and decrease the application of suction at the drain catheter.

In the above-described embodiments of the invention, fluid aspirated from the wound may be dispensed in a container. A rotor may further separate the aspirated fluid into two or more components.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

In illustrative embodiments, a wound drainage system that includes a drain catheter and a controller for aspirating fluids from a wound is presented. The system allows for intermittent relaxation of, thus helping to unclog and/or prevent obstruction of the drain catheter. Details are discussed below.

Figure 1:
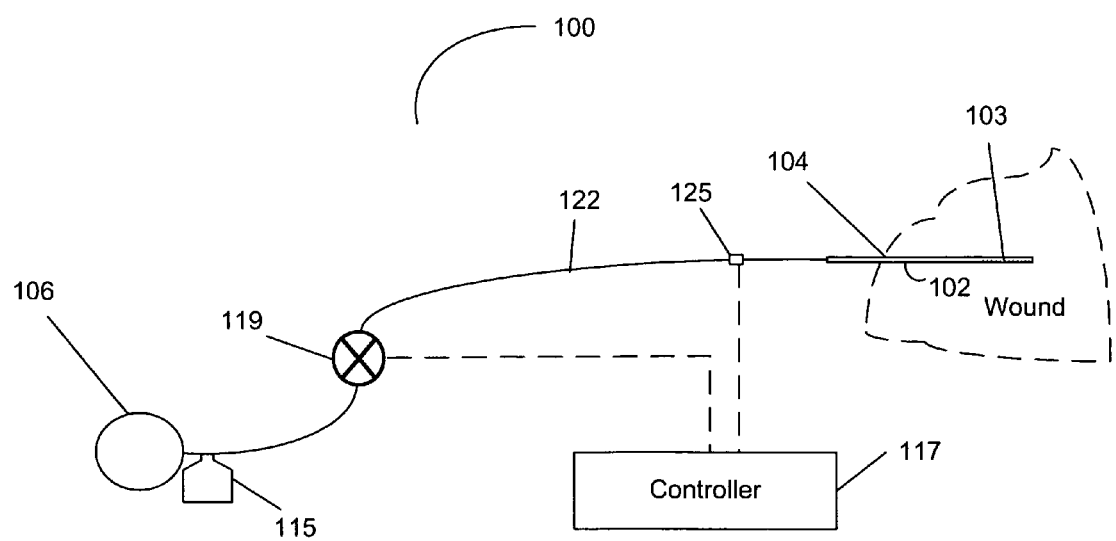
FIG. 1 is a illustration of a wound drainage system, in accordance with one embodiment of the invention.

FIG. 1 is a illustration of a wound drainage system 100, in accordance with one embodiment of the invention. The system 100 includes a drain catheter 102 that generally includes a tubular body 104 defining at least one lumen through which fluid may pass. At a first end of the tubular body 104 are one or more perforations 103. Fluid from the wound, which may be, without limitation, a surgical site, is allowed to enter the tubular body 104 through the perforations 103, and can be drawn away from the wound though at least one lumen of the tubular body 104. In various embodiments, the drain catheter 102 may also include additional lumen to allow for passage of other fluids or gases to or from the wound. For example, additional lumen may be utilized to provide various drugs to the wound.

The drain catheter 102 may be of various size and shape and constructed of a soft, flexible, biocompatible material. For example, the drain catheter 102 may be made of, without limitation, a polymeric material, such as polyethylene, polypropylene, polybutylene, polystyrene, polyvinyl chloride, polyvinylidene fluoride, polytetrafluoroethylene, polyurethane, silicone elastomer, polybutadiene copolymer elastomer, and/or polycarbonate. In various embodiments, the drain catheter may also be coated with a hydrophilic coating that provides minimal friction when wet.

The drain catheter 102 is placed in fluid communication with a suction device 106 via a conduit 122, which may be, without limitation, plastic tubing. The suction device 106 provides a region of low pressure such that fluid is drawn into the drain catheter 102 towards the suction device 106. The suction device 106 may be, without limitation, a pump or a bellows apparatus that creates a vacuum or partial vacuum. In other embodiments, the suction device 106 may be provided through a wall vacuum port that is part of a facility wide source of vacuum available, for example, in many hospitals. Any fluid aspirated from the wound may be collected, for example, in an in-line container 115.

When in use, the drain catheter 102 is positioned such that the first end is placed adjacent to the wound. Suction provided by the suction device 106 causes fluids and/or other material from the wound to be aspirated through the perforations 103 in the tubular body 104 into the drain catheter 102 and further into the container 115.

In accordance with various embodiments of the invention, a controller 117 periodically increases and decreases application of suction at the drain catheter 102. Periodically decreasing the application of suction at the drain catheter 102 allows the surrounding tissue to relax, helping to clear the drain catheter's perforations 103. In various embodiments, the controller 117 may control both the magnitude and associated time of the applied suction. In other embodiments, the controller 117 may control when suction is applied at the drain catheter 102, with the amount of suction being held substantially constant.

The controller 117 may cyclically control application of suction at the drain catheter 102 such that suction is applied at the drain catheter 102 for a first predetermined amount of time to allow for drainage of fluid through the drain catheter 102, and interrupted or sufficiently decreased (compared to the level of suction during the first predetermined amount of time), to allow for relaxation of the tissue, for a second predetermined amount of time. For example, the controller 117 may cyclically cause application of suction at the drain catheter 102 for ten minutes, and interrupt suction for 30 seconds. The amount of suction to be applied during the first predetermined amount of time and/or the second predetermined time can vary between and within cycles. Additionally, the first predetermined amount of time and/or the second predetermined amount of time may fluctuate over time or remain constant. The amount of suction to be applied, the first predetermined amount of time, and/or the second predetermined amount of time may be variably controlled, stored in memory and/or entered at a suitable user interface. Note that in various embodiments, the amount of time suction is applied to the wound may not be predetermined. For example, the controller 117 may cyclically increase and decrease the application of suction at the wound drain as a function of pressure within the conduit 122.

The controller 117 may include, without limitation, a circuit, such as a timer circuit, and/or a Central Processor Unit (CPU) that may include memory and be appropriately preprogrammed or configured to be loaded with an appropriate program. Memory may include, for example, a diskette, a fixed disk, a Compact Disk (CD), Read Only Memory (ROM), Erasable Programmable Read-Only Memory (EPROM), and/or Random Access Memory (RAM). In various embodiments, the controller may include mechanical means, such as a mechanical timer.

In the depicted embodiment, the controller 117 provides control signals to a valve means 119 that is in fluid communication with the drain catheter 102 and the suction device 106. The valve means 119 may be electrically and/or mechanically controlled by the controller 117 to variably limit the application of suction at the drain catheter 102. For example, the valve means 119 may be controlled via, without limitation, a solenoid or a cam device.

The valve means 119 may include, without limitation, a vent valve 119 that may be positioned within the conduit 122. The vent valve selectively opens (fully or partially) to allow conduit 122 to vent to the atmosphere, thereby decreasing the amount of suction applied at the drain catheter 102. The vent valve may include a filter, such as, but not limited to a bacterial filter, for preventing introduction of outside contaminants into the conduit system 122 which may adversely affect the wound. In other embodiments, the valve means 119 may include a clamp, or other device capable of regulating suction within the conduit 122. The clamp may be positioned, for example, in a conduit that branches off from the conduit connecting the suction device 106 and the drain catheter 102, and which places the conduit 122 in fluid communication with the outside environment when released. Similar to the vent valve, the clamp may also be used in combination with a suitable filter to prevent contaminants from entering the conduit 122.

In various embodiments, the controller 117 may receive information from one or more sensors 125. The one or more sensors 125 may include, for example, a conventional pressure transducer that provides a signal representative of pressure within the conduit 122. Based on the signal received from the one or more sensors 125, the controller 117 may verify and/or adjust the level of suction generated by the suction device 106 and/or that is applied at the drain catheter 102.

Figure 2:
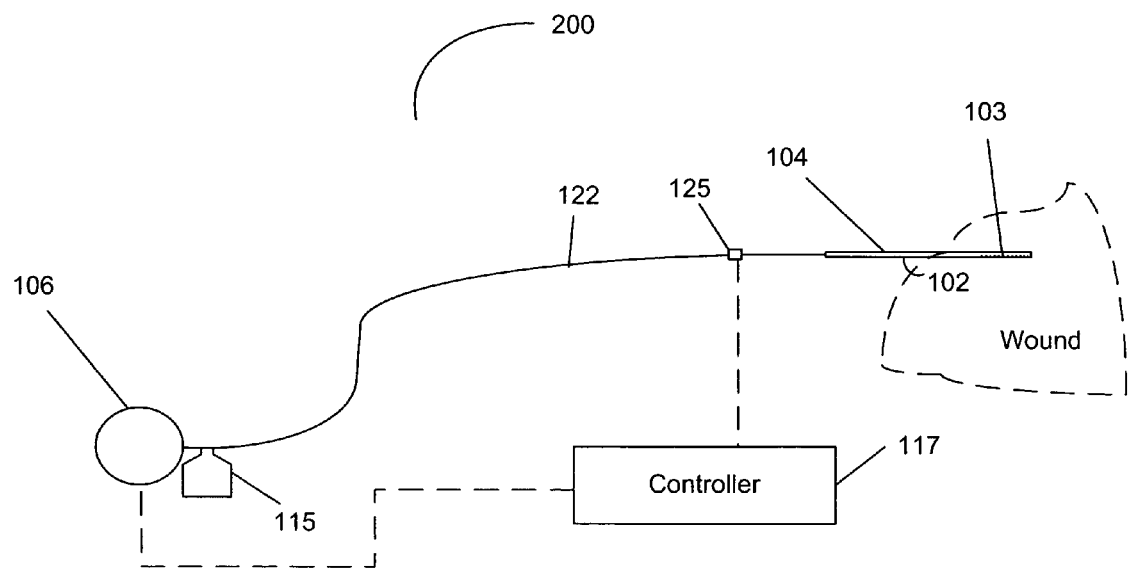
FIG. 2 is an illustration of a wound drainage system in which the controller controls a suction device to periodically increase and decrease the application of suction at a drain catheter, in accordance with one embodiment of the invention.

FIG. 2 is an illustration of a wound drainage system 200 in which the controller 117 controls the suction device 106, as opposed to, or in addition to a valve means, to periodically increase and decrease the application of suction at a drain catheter 102, in accordance with one embodiment of the invention. More particularly, the controller 117 may provide, without limitation, mechanical or electrical control signals to the suction device 106 that control the amount of suction generated by the suction device 106. For example, the controller 117 may control the suction device 106, such as a pump, to cyclically turn on or off, or otherwise cyclically increase or decrease the generated amount of suction.

The above-described wound drainage systems 100 and 200 may be used in combination with a rotor to separate fluid suctioned by the drain catheter into two more components. In various embodiments, the rotor may also act as a source of suction at the drain catheter. The rotor may be of various types, such as described in U.S. Pat. No. 5,733,253 and U.S. Pat. No. 5,651,766, which are incorporated herein, in their entireties, by reference.

Figure 3:
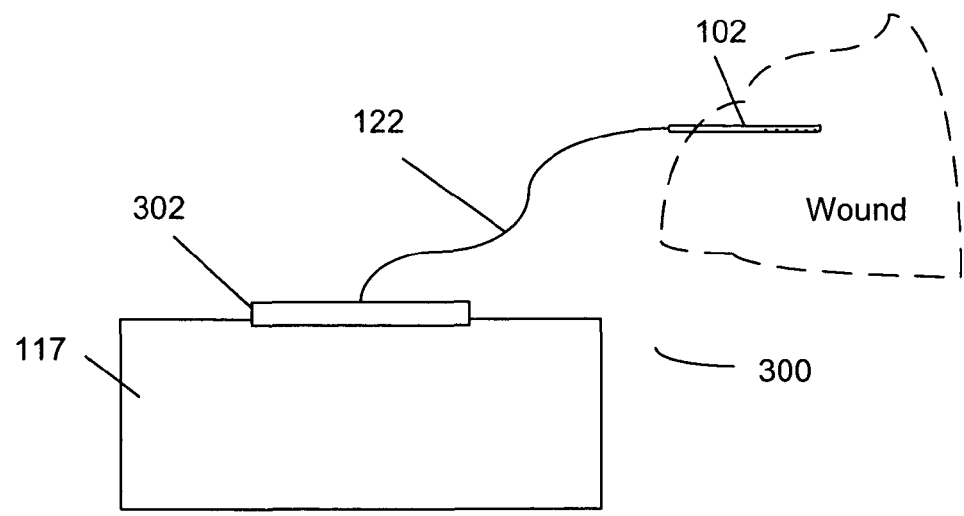
FIG. 3 is an illustration of a system for recovering blood or other fluids from a wound site, and for further separating the blood into one or more components, in accordance with one embodiment of the invention.

FIG. 3 shows a system 300, according to the present invention, for recovering blood or other fluids from a wound site, and for further separating the blood into one or more components. The system includes a drain catheter 102 that is coupled to a variable-volume rotor 302 via tubing 122. The drain catheter 102, variable-volume rotor 302, and tubing 122 may form a disposable set in which fluids are collected and processed. The disposable set may also include various storage containers for storing, without limitation, anticoagulant or one of the separated components, and appropriate valving to direct the fluid in the desired manner.

A vacuum created in the rotor 302 causes suction to be applied to the drain catheter 102, such that fluid can be drawn from the wound, as described below in more detail. A controller 117, which is preferably a digital data processor, interfaces with the disposable set and controls the collection and separation process. In accordance with various embodiments of the invention, the controller 117 increases and decreases the application of suction at the drain catheter 102, so as to periodically relax tissue adjacent the drain catheter 102.

Figure 4:
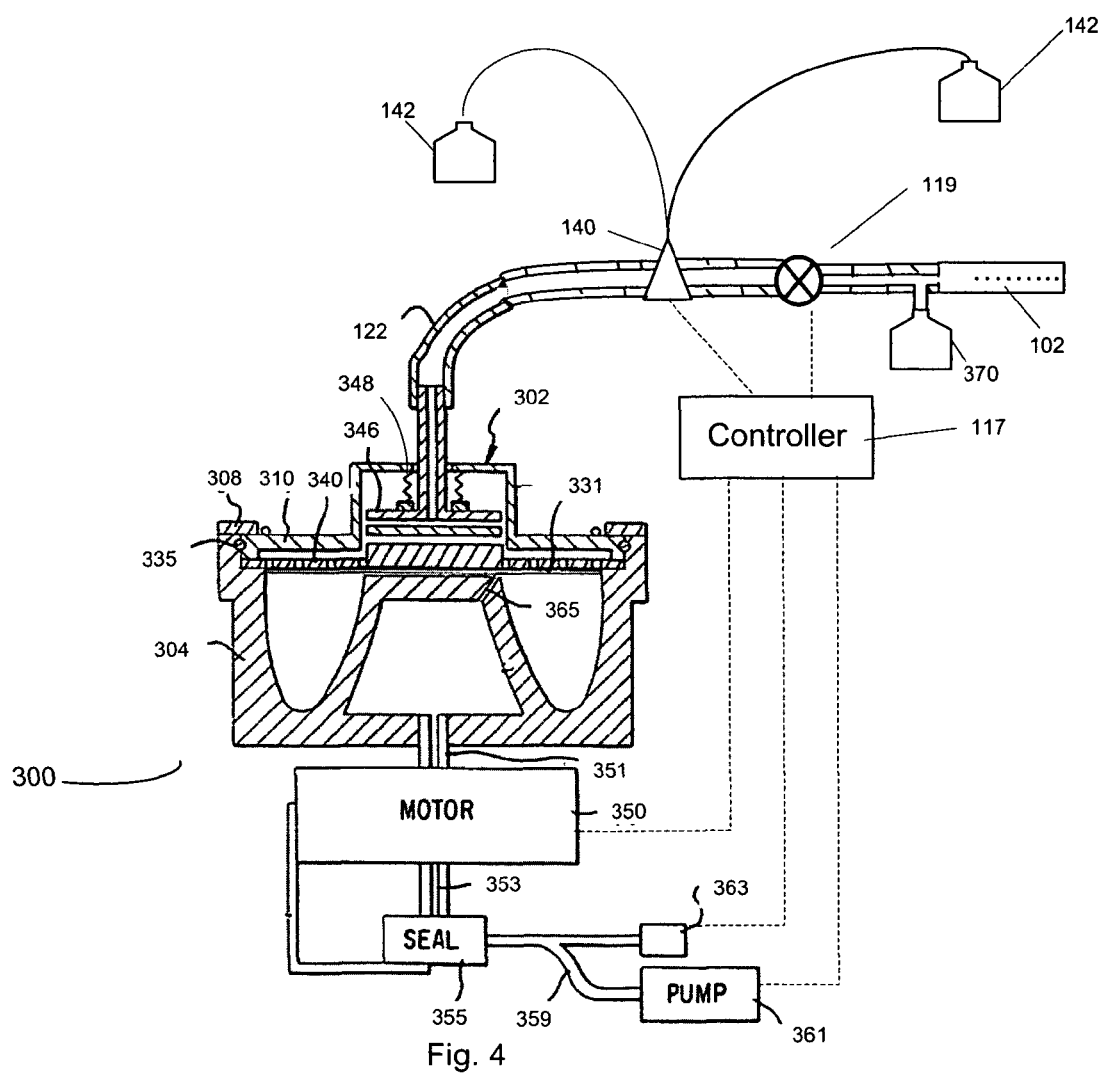
FIG. 4 illustrates in more detail the embodiment shown in FIG. 3, in accordance with one embodiment of the invention.

FIG. 4 illustrates portions of the system 300 in more detail, in accordance with one embodiment of the invention. The variable-volume rotor 302 illustrated is of a type described in U.S. Pat. No. 5,733,253 at FIGS. 1-4, although other rotors shown and described in this patent may be used as well, such as the rotors shown in FIG. 7, 8A, or 41 and 42. The variable-volume rotor 302 has an elastic diaphragm 331 and a rigid member 310, which together define a chamber of varying volume, as described in U.S. Pat. No. 5,733,253. Fluid communication in and out of the rotor is provided by a collector assembly 346 which is attached to tubing 122 and is connected to the rigid member 310 via a rotary seal 348. The tubing 122 and the collector assembly 346 are held stationary while the rest of the variable-volume rotor 302 rotates (i.e., the rigid wall 310 and the diaphragm 331). To protect the elastic diaphragm 331 while spinning from the stationary collector assembly 46, a perforate interior wall 340 is attached below the rigid wall 310. The perforate interior wall 340 includes holes that allow fluid communication between the areas of the chamber above and below the perforate interior wall 340.

In use, the variable volume rotor 302 is held onto and spun by a centrifuge chuck 304. The chuck 304 holds the rotor 302; the chuck 304 has a clamp 308 that holds the rotor 302 securely in place in the chuck 304, and an O-ring 335 that forms an air-tight seal. A drive motor 350 is connected to the chuck 304 by means of a shaft 351. In order to apply a vacuum or pressure to the rotor 302 to pump fluid in and out of the rotor, respectively, the shaft 351 has an axial hole through its center 353 and is connected to a rotary pneumatic seal 355, which in turn is connected by tubing 359 to a compressor/vacuum pump 361 and to a controllable exhaust valve 363. Holes 365 in the interior of the chuck 304 allow air to flow to and from the compressor/vacuum pump 361. These spinning and pumping mechanisms are controlled by the controller 117.

To draw blood from the wound, controller 117 controls the compressor/vacuum pump 361 to provide a vacuum through the chuck to the exterior side of the diaphragm 331. Because the diaphragm 331 is pulled downward by the vacuum in the chuck 304, an area of low pressure is created in the chamber, causing suction to be applied at the drain catheter 102. Consequently, fluid is drawn into the rotor 302 through the rotor tube 122. As more and more fluid enters the rotor 302, the diaphragm 331 changes shape to accommodate it. In this manner, blood and/or other fluid is drawn from the wound-drain site through the drain catheter 112 and associated tubing 122/valving 149 into the rotor 302.

Similar to above-described embodiments of the invention, the controller 117 increases and decreases the application of suction at the drain catheter 102, so as to periodically relax the tissue adjacent the drain catheter 102. Controller 117 may, for example, vary the amount of suction applied at the drain catheter 112 by providing appropriate control signals to the compressor/vacuum pump 361 to cyclically increase and decrease the vacuum seen by the exterior side of the diaphragm 331. In other embodiments, the controller 112 may control a valve 119, such as a vent valve, that may be positioned in the tubing 122 between the drain catheter 112 and the rotor 302. Variations in the suction applied at the drain catheter 112 can be accomplished by opening or closing the vent valve 119 while applying a vacuum to the exterior side of the diaphragm 331. The vent valve 119 may include a bacterial filter to prevent contaminants from entering tubing 122.

In various embodiments, an intermediate wound-drain canister 370 may be placed in the line 122 between the drain catheter 112 and the rotor 302. A filter may be located adjacent to or in this canister 370 to filter undesirable components from the fluid prior to entry into the rotor 302, and anticoagulant may be added to the blood in the canister 370. Such a canister 370 can hold the whole blood pulled from the wound until the blood is to be processed; at that time, the vacuum generated in the chuck or a pump may be used to pull the blood from the canister to the rotor 302.

In preferred embodiments, the wound-drain canister 370 is positioned, without limitation, between the valve 119 and the drain catheter 102. When fluid is being aspirated from the wound into the canister 370, the vent valve 119 can be periodically opened without regard to fluid exiting the valve 119 and/or polluting the valve's bacterial filter. When aspirating the fluid from the canister 370 into the rotor 302, the vent valve 119 can remain closed, since the drain catheter 102 is typically removed from the wound at this point and tissue ingrowth is no longer a concern.

When it is desired to separate the blood and/or other fluid in the rotor 302, the chuck spins the body of the rotor 302. In various embodiments, fluid flow to the rotor 302 may be stopped when the desired or the available amount of blood has entered the rotor 302, or when it is full. Since the processing chamber has a variable volume, the rotor 302 does not have to be filled to its capacity with blood for the process to be done properly. After the flow into the rotor 302 is stopped, the blood is then subjected to centrifugal force as long as is appropriate to separate the various components, similar to the manner described in above-referenced patent to U.S. Pat. No. 5,733, 253.

When separation is complete, the pump/compressor 361 begins to pump compressed air into the chuck 304. The compressed air first pushes the fluid element with the lightest specific gravity out of the processing area. The lighter fluid passes through those holes in the plate 340 at the smallest radius not sealed by the diaphragm 331. Each blood element in turn by specific gravity flows through the holes in the plate 340 at the smallest radius not yet sealed by the diaphragm 331 and then out of the rotor 302.

The blood elements exiting the rotor can be diverted as desired by the valve 140. The fluid flowing out of the rotor's processing chamber may be diverted to a specific container 142 (e.g., a waste bag or an RBC bag) or returned to a donor depending on the purpose of the process, on how the system is configured and on how the valve 140 or other tubing directs the fluids.

For example, in a typical post-operative salvage process, the lighter elements—most of the plasma and platelets—are considered waste and are sent through the valve 140 and the tubing 122 to a waste bag. The remaining blood elements—mostly concentrated RBCs—may then be further processed in the rotor 302 and then forced out of the rotor 302 through the valve 140 and the tube 122 to an RBC bag. After a sufficient amount of RBCs are sent to the RBC bag, the RBC bag is disconnected from the valve 140 and may then be attached to the patient in order to return the patient's RBCs.

Alternative embodiments of the invention, such as the controller 117, may be implemented as, or otherwise include, a computer program product for use with a computer system. Such implementation may include a series of computer instructions fixed either on a tangible medium, such as a computer readable media (e.g., a diskette, CD-ROM, ROM, or fixed disk), or fixed in a computer data signal embodied in a carrier wave that is transmittable to a computer system via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

What is claimed is:

1. A wound drainage system for draining fluid from a patient comprising:
    a drain catheter
    a suction means for applying suction at the drain catheter; and
    an automated controller configured for automatically periodically increasing and decreasing the application of a suction at the drain catheter such that suction is applied at the drain catheter for a first predetermined amount of time and interrupted at the drain catheter for a second predetermined amount of time and the amount of suction applied during the first period of time is varied.

2. The wound drainage system according to claim 1, further comprising valve means, the valve means positioned between the drain catheter and the suction means, wherein the controller controls the valve means to periodically increase and decrease the application of suction at the drain catheter.

3. The wound drainage system according to claim 2, further comprising a conduit in fluid communication with the suction means and the drain catheter, wherein the valve means is disposed in the conduit.

4. The wound drainage system according to claim 2, wherein the valve means includes a vent valve.

5. The wound drainage system according to claim 1, wherein the suction means includes a pump.

6. The wound drainage system according to claim 5, wherein the controller controls the pump to periodically turn on and off.

7. The wound drainage system according to claim 1, further comprising a container for dispensing fluid aspirated from the wound.

8. The wound drainage system according to claim 1, wherein the controller includes a computer readable medium encoded to perform a method, the method comprising periodically increasing and decreasing the application of suction at the drain catheter.

9. The wound drainage system according to claim 1, further comprising a rotor for receiving fluid suctioned by the drain catheter, the rotor for separating fluid suctioned by the drain catheter into two or more components.

10. The wound drainage system according to claim 1, wherein the suction means provides one of a vacuum and a partial vacuum.

11. A wound drain system for implantation into and for drainage of fluid from a wound of a patient comprising:
    a drain catheter;
    a suction device;
    a conduit in fluid communication with the suction device and the drain catheter;
    a valve disposed at the conduit; and
    an automated controller configured for automatically variably controlling the valve to periodically increase and decrease the application of suction at the drain catheter such that suction is applied at the drain catheter for a first predetermined amount of time and interrupted at the drain catheter for a second predetermined amount of time and the amount of suction applied during the first period of time is varied.

12. The wound drainage system according to claim 11, wherein the valve includes a vent valve.

13. The wound drain system according to claim 11, wherein the suction device is a pump.

14. The wound drainage system according to claim 11, further comprising a container for dispensing fluid aspirated from the wound.

15. The wound drainage system according to claim 11, wherein the controller includes a computer readable medium encoded to perform a method, the method comprising controlling the valve so as to periodically increase and decrease the application of suction at the drain catheter.

16. The wound drainage system according to claim 11, further comprising a rotor for receiving fluid suctioned by the drain catheter, the rotor for separating fluid suctioned by the drain catheter into two or more components.

17. A wound drainage system for draining fluid from a wound of a patient comprising:
a drain catheter
a suction source for applying suction at the drain catheter; and
an automated controller configured for automatically controlling the suction source so as to periodically increase and decrease the application of suction at the drain catheter such that suction is applied at the drain catheter for a first predetermined amount of time and interrupted at the drain catheter for a second predetermined amount of time and the amount of suction applied during the first period of time is varied.

18. The wound drainage system according to claim 17, wherein the suction source is a pump.

19. The wound drain system according to claim 18, wherein the controller controls the pump to periodically turn on and off.

20. The wound drainage system according to claim 17, further comprising a container for dispensing fluid aspirated from the wound.

21. The wound drainage system according to claim 17, wherein the controller includes a computer readable medium encoded to perform a method, the method comprising controlling the suction source so as to periodically increase and decrease the application of suction at the drain catheter.

22. The wound drainage system according to claim 17, further comprising a rotor for receiving fluid suctioned by the drain catheter, the rotor for separating fluid suctioned by the drain catheter into two or more components.

23. A wound drainage system for draining fluid from a patient comprising:
a drain catheter,
means for applying suction at the drain catheter; and
means for automatically periodically increasing and decreasing the application of suction at the drain catheter such that suction is applied at the drain catheter for a first predetermined amount of time and interrupted at the drain catheter for a second predetermined amount of time and the amount of suction applied during the first period of time is varied.

* * * * *